(12) United States Patent
Williams et al.

(10) Patent No.: US 8,927,480 B2
(45) Date of Patent: Jan. 6, 2015

(54) CLEANING CLOTH WITH ENCAPSULATED FORMULATION, STEAM MOP AND METHOD

(75) Inventors: Jesse J. Williams, Zeeland, MI (US); Jeffrey A. Scholten, Ada, MI (US); Jay M. Kellis, Grand Rapids, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 488 days.

(21) Appl. No.: 13/323,286

(22) Filed: Dec. 12, 2011

(65) Prior Publication Data

US 2012/0145191 A1    Jun. 14, 2012

Related U.S. Application Data

(60) Provisional application No. 61/422,765, filed on Dec. 14, 2010.

(51) Int. Cl.
  *A47L 13/20* (2006.01)
  *A47L 13/17* (2006.01)
  *A47L 13/22* (2006.01)
  *A61L 9/03* (2006.01)
  *C11D 17/04* (2006.01)
  *C11D 17/00* (2006.01)

(52) U.S. Cl.
  CPC .................. *A47L 13/17* (2013.01); *A47L 13/20* (2013.01); *A47L 13/225* (2013.01); *A61L 9/03* (2013.01); *C11D 17/049* (2013.01); *C11D 17/0039* (2013.01)
  USPC .............................. 510/295; 401/268; 15/228

(58) Field of Classification Search
  CPC ....... A47L 13/22; A47L 13/225; A47L 13/20; C11D 17/049; C11D 3/505
  USPC .............................. 15/320; 510/295; 401/268
  See application file for complete search history.

(56) References Cited

U.S. PATENT DOCUMENTS

| | | | |
|---|---|---|---|
| 3,283,357 A | 11/1966 | Decker et al. | |
| 4,971,471 A | 11/1990 | Sloan | |
| 7,163,349 B2 * | 1/2007 | Policicchio et al. | 401/137 |

(Continued)

FOREIGN PATENT DOCUMENTS

| | | |
|---|---|---|
| EP | 1980192 A2 | 10/2008 |
| EP | 2329755 A2 | 6/2011 |

(Continued)

OTHER PUBLICATIONS

Markus Masset, Partial European Search Report, Feb. 24, 2014, 6 pages, Munich, Germany.

(Continued)

*Primary Examiner* — Gregory Webb
(74) *Attorney, Agent, or Firm* — McGarry Bair PC

(57) ABSTRACT

A cleaning cloth for use with a steam mop having a housing mounting the cleaning cloth for cleaning the surface to be cleaned and a steam delivery system for delivering steam to the cleaning cloth. The cleaning cloth has at least one fabric layer that is configured to be attached to a steam mop and an encapsulated cleaning composition associated with the fabric layer and configured to be released by exposure to steam delivered to the cleaning cloth. A steam mop for use of the cleaning cloth and a method of cleaning with the cleaning pad is also disclosed.

28 Claims, 6 Drawing Sheets

(56) References Cited

U.S. PATENT DOCUMENTS

| | | |
|---|---|---|
| 7,182,537 B2 | 2/2007 | Policicchio et al. |
| 7,357,949 B2 | 4/2008 | Trogolo et al. |
| 7,661,212 B2 | 2/2010 | Hahn |
| 2002/0168216 A1* | 11/2002 | Policicchio et al. .......... 401/270 |
| 2002/0174863 A1 | 11/2002 | Saric et al. |
| 2003/0027473 A1 | 2/2003 | Kakiuchi et al. |
| 2004/0144406 A1* | 7/2004 | Garabedian et al. ............ 134/26 |
| 2005/0153857 A1* | 7/2005 | Sherry et al. ................. 510/295 |
| 2005/0155628 A1 | 7/2005 | Kilkenny et al. |
| 2005/0155631 A1* | 7/2005 | Kilkenny et al. ................ 134/6 |
| 2005/0217698 A1 | 10/2005 | Mitchell et al. |
| 2006/0171764 A1 | 8/2006 | Hoadley |
| 2007/0131248 A1 | 6/2007 | McKechnie |
| 2010/0107351 A1* | 5/2010 | Rosenzweig et al. ........ 15/209.1 |
| 2010/0186463 A1* | 7/2010 | Vrdoljak et al. ................ 68/222 |
| 2010/0287716 A1* | 11/2010 | Kasper et al. ..................... 15/4 |
| 2011/0131753 A1* | 6/2011 | Krebs ............................ 15/320 |
| 2012/0137465 A1* | 6/2012 | Nolan et al. .................... 15/321 |

FOREIGN PATENT DOCUMENTS

| | | |
|---|---|---|
| JP | 2003284659 A | 10/2003 |
| WO | 9842819 A1 | 10/1998 |
| WO | 0152714 A1 | 7/2001 |
| WO | 2006008461 A1 | 1/2006 |
| WO | 2010078513 A1 | 7/2010 |

OTHER PUBLICATIONS

Aditya Angadi, Melbourne Patent Examination Centre, Patent Examination Report No. 1, Nov. 21, 2013, 5 pages, Australian Government, Woden Australia.

Markus Masset, European Search Report, May 23, 2014, 14 pages, Munich.

* cited by examiner

CLEANING CLOTH WITH ENCAPSULATED FORMULATION, STEAM MOP AND METHOD

CROSS-REFERENCE TO RELATED APPLICATION

This application claims the benefit of U.S. Provisional Application No. 61/422,765, filed Dec. 14, 2010, which is incorporated herein by reference in its entirety.

BACKGROUND OF THE INVENTION

Steam mops are well known devices for cleaning bare floor surfaces, such as tile, linoleum, vinyl, laminate, and hardwood floors. Typical steam mops have a reservoir for storing water that is fluidly connected to a selectively engageable pump or valve. The pump or valve outlet is fluidly connected to a steam boiler with a heating element to heat the water. The steam boiler generates steam, which is directed towards the cleaning surface through a nozzle or manifold mounted in the foot. Steam is typically applied to the backside of a mop pad or cloth attached to the foot. Steam vapor eventually saturates the entire pad as the moisture wicks outwardly from the point of steam application. The damp pad is wiped across the surface to be cleaned to remove dirt, dust, and debris present on the cleaning surface.

A bare floor cleaner has heretofore been sold in the United States by BISSELL Homecare, Inc. under the mark Steam Mop™. The Steam Mop™ bare floor cleaner comprises a base assembly and an upright handle pivotally mounted to the base assembly. The base assembly includes a base housing with a fluid distributor for distributing fluid to the surface to be cleaned and a mop pad that is affixed beneath the base housing and positioned for contacting the surface to be cleaned. The upright handle includes a handle housing, a water tank mounted to the handle housing and adapted to hold a quantity of water, a fluid distribution system between the water tank and the base housing fluid distributor for distributing fluid from the water tank to the mop pad for applying the steam to the surface to be cleaned, and a heating element within the fluid distribution system for heating the water from the water tank to steam.

During use, the mop pad eventually becomes saturated with liquid and soiled with embedded dirt, dust, and debris. The soiled mop pad can be laundered and re-used. A mop pad can generally be used for one or two steam mopping sessions prior to being laundered.

SUMMARY OF THE INVENTION

According to the invention, a cleaning cloth for use with a steam mop has at least one fabric layer that is configured to be attached to a steam mop and an encapsulated cleaning composition associated with the fabric layer and configured to be released from the encapsulation by exposure to steam delivered to the cleaning cloth. The steam mop may have a housing mounting the cleaning cloth for cleaning the surface to be cleaned and a steam delivery system for delivering steam to the cleaning cloth.

In one embodiment, the at least one fabric layer comprises two fabric layers that form a pocket and the encapsulated cleaning composition is positioned in the pocket. The at least one fabric layer can further comprises a cover for closing an opening to the pocket. The at least one fabric layer can comprises a lower fabric layer and an upper fabric layer, and the encapsulated cleaning composition can be positioned between the upper and lower fabric layers. Further, the lower fabric layer can be textured to increase friction with the surface to be cleaned. Further, the upper fabric layer can be joined with the lower fabric layer at one edge to form a flap that is separable from the lower layer. The flap and lower fabric can include a hook and loop fastener combination between two.

In another embodiment, the encapsulated cleaning composition is embedded within or attached to the at least one fabric layer. In addition, the encapsulated cleaning composition can include a cleaning composition embedded within a water-soluble polymer film, which is mounted to the at least one fabric layer. The film can be mounted by one of thermal bonding, ultrasonic bonding, adhesive bonding, hot melt adhesive, dissolvable adhesive, or laminating.

The encapsulated cleaning composition can comprise a disinfecting or sanitizing agent having anti-bacterial, anti-viral, miticidal, germicidal, anti-fungal or anti-microbial properties. In addition, the disinfecting or sanitizing agent can comprise an EPA-exempted natural disinfectant. In addition, the disinfecting or sanitizing agent can comprise one of: quaternary ammonium compounds (quats), such as Dialkyl quats, Dialkyl blend quats, single-chain quats and dual chain quats, hydrogen peroxide or hydrogen peroxide derivatives, or colloidal particles with disinfecting or sanitizing properties, including silver and/or copper. In addition, the encapsulated cleaning composition can comprise at least one of a fragrance, an odor-eliminating agent, or an odor control agent. In addition, the encapsulated cleaning composition can comprise at least one floor care component, including floor polish, polymer protectant, anti-streaking components, or vinegar.

In another embodiment, the encapsulated cleaning composition is bonded, affixed or in register with the at least one fabric layer. In addition, the encapsulated cleaning composition can be embodied in at least one of a film, a wafer, a pouch, a sachet, or a granulated composition. In addition, the wafer can be a fragrance-infused thermoplastic sheet and the fragrance can be volatilized into the cleaning cloth and surrounding atmosphere when the at least one fabric layer is exposed to steam. In addition, the wafer can comprise multiple perforations to pass steam through the cleaning composition. In addition, the wafer can be a porous plastic sheet and the cleaning composition can be released from the perforations into the cleaning cloth and surrounding atmosphere when the wafer is exposed to steam.

In an alternative embodiment, the encapsulated composition comprises a gel contained within a heat- and/or moisture-soluble barrier.

Alternatively, the barrier comprises one of vinyl alcohol-vinyl acetate copolymer, polyvinyl alcohol polymer, or octenylsuccinates-starch polymer.

In a preferred embodiment, the encapsulated cleaning composition is released only upon reaching a temperature of at least about 80° C.

Further according to the invention, a steam mop comprises a housing for movement along a surface to be cleaned, a cleaning cloth as described above is coupled with the housing for cleaning the surface to be cleaned, and a steam delivery system for delivering steam to the cleaning cloth. In one embodiment, the housing comprises a foot assembly for movement along a surface to be cleaned and a handle assembly mounted to the foot assembly. The cleaning cloth can be mounted to the foot assembly.

Further according to the invention, a method for cleaning a surface comprises applying to the surface a cleaning cloth with a cleaning composition encapsulated within a heat-activated barrier and delivering steam to the cleaning cloth to release the cleaning composition from within the heat-activated barrier for application onto the surface.

DESCRIPTION OF THE PREFERRED EMBODIMENT

Figure 1:
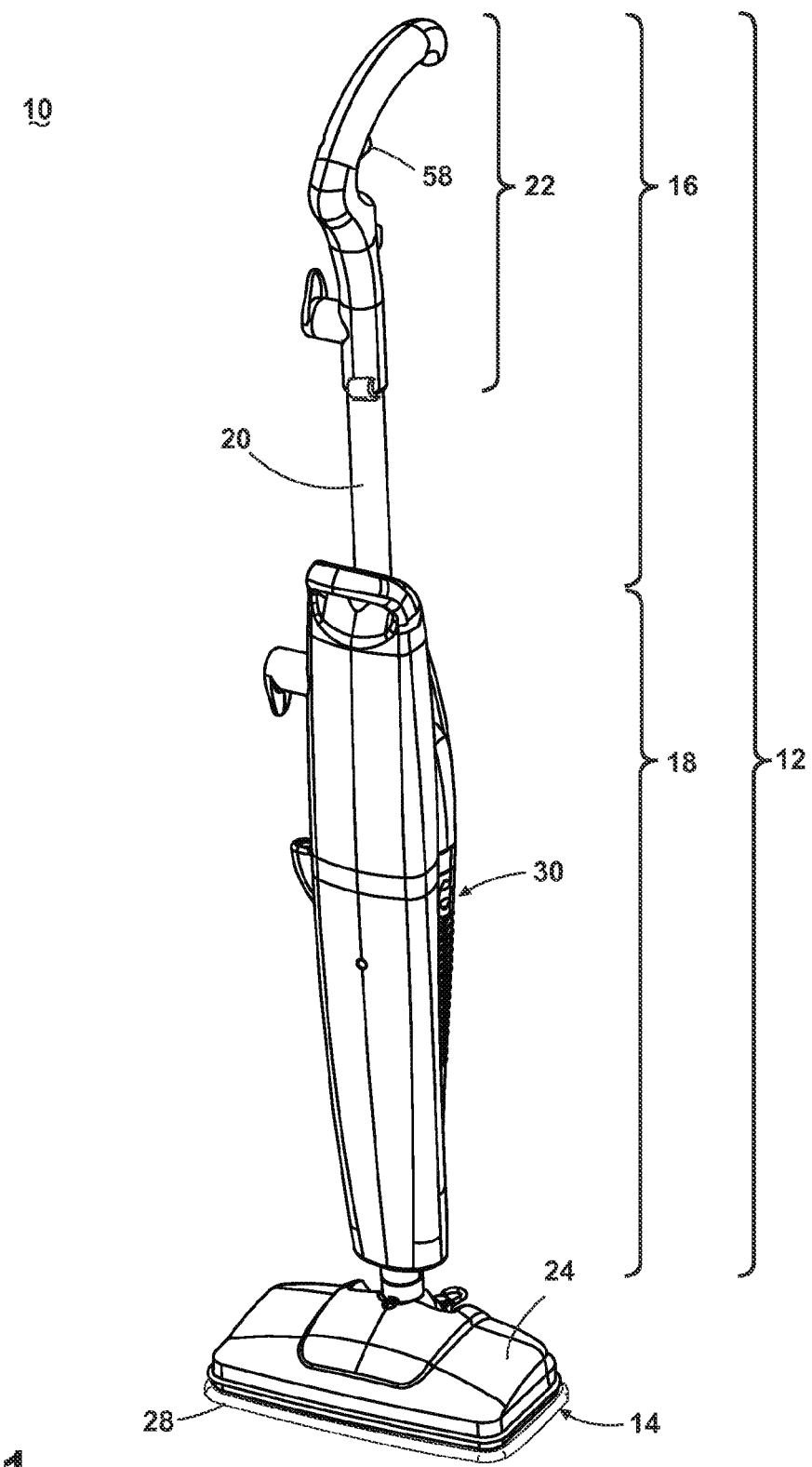
FIG. 1 is a front perspective view of an upright steam mop according to an embodiment of the invention.

The invention relates to a cleaning cloth that can be removably mounted to an otherwise conventional steam mop as illustrated in FIG. 1. A steam mop 10 described herein can share many features of a traditional steam mop, which will not be described in detail except as necessary for a complete understanding of the invention. Examples of suitable steam mops which may be used with the embodiments of the invention described herein include the Steam Mop™, sold in the United States by BISSELL Homecare, Inc. and International Application No. PCT/US10/45167, filed Aug. 11, 2010, titled "Upright Steam Mop with Auxiliary Hand Tool" and U.S. application Ser. No. 12/778,615, filed May 12, 2010, titled "Upright Steam Mop Sweeper", both of which are assigned to BISSELL Homecare Inc. and which are herein incorporated by reference in their entirety.

The steam mop 10 can comprise an upright handle assembly 12 and a base or foot 14 pivotally mounted to the handle assembly 12. The handle assembly 12 can pivot from an upright or vertical position, where the handle assembly 12 is substantially vertical relative to a surface to be cleaned, to a lowered position, whereby the handle assembly 12 is rotated in a rearward direction relative to the foot 14 to an acute angled relative to the surface to be cleaned. The steam mop 10 is adapted to glide across the floor or other hard surface on the foot 14.

The handle assembly 12 comprises an upper handle assembly 16 and a lower handle assembly 18. The upper handle assembly 16 comprises a hollow handle tube 20 having a grip assembly 22 fixedly attached to a first end of the handle tube 20 and the lower handle assembly 18 fixedly attached to a second end of the handle tube 20 via screws or other suitable commonly known fasteners. The grip assembly 22 has an arcuate grip portion; however, it is within the scope of the invention to utilize other grips commonly found on other machines, such as closed-loop grips having circular or triangular shapes.

The lower handle assembly 18 and/or the foot 14 can further include a fluid distribution system 30. The fluid distribution system 30 can be primarily located within the lower handle assembly 18, although it is also within the scope of the invention for all or a portion of the fluid distribution system 30 to be located within the foot 14.

Figure 2:
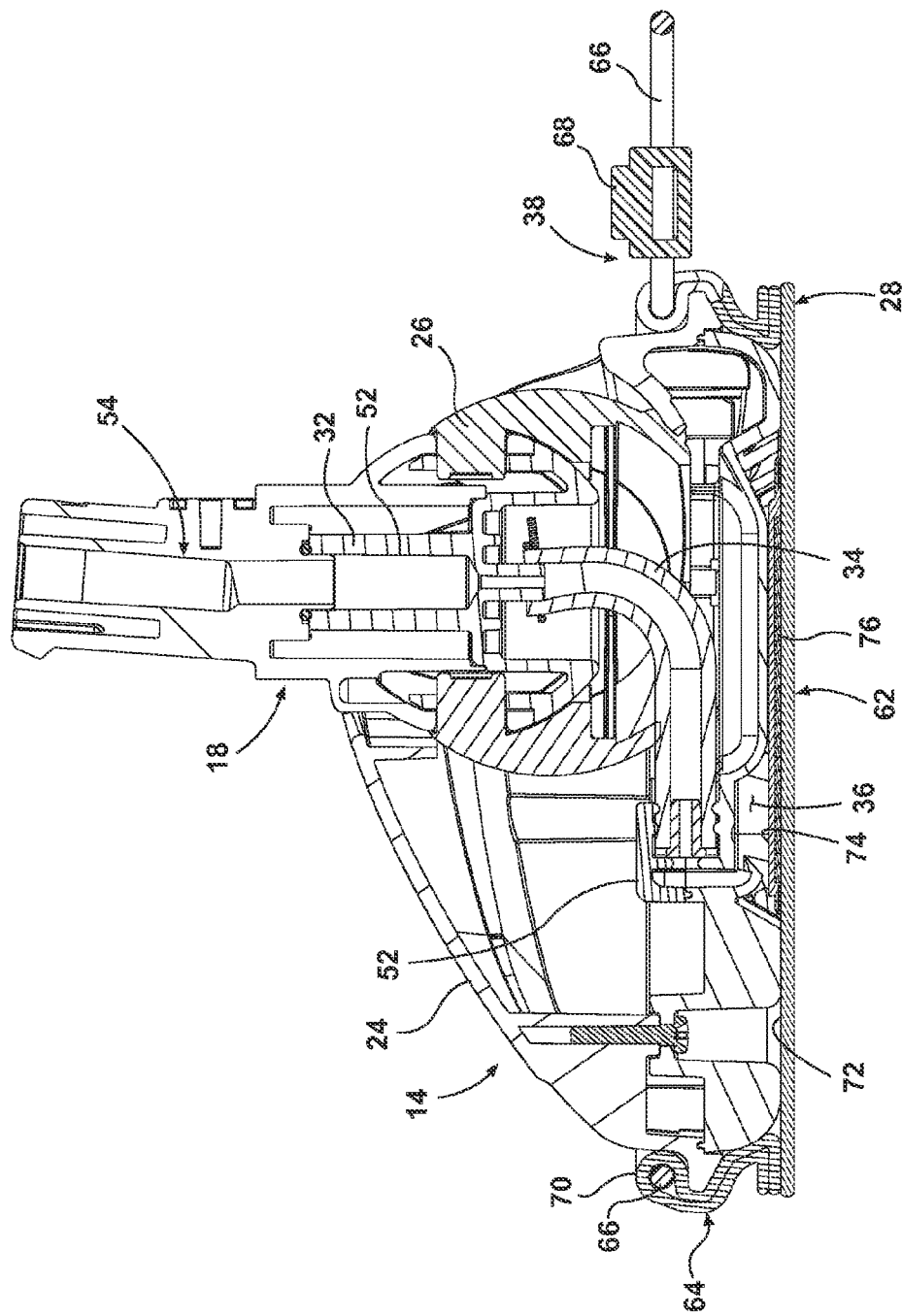
FIG. 2 is a cross-sectional view through line 2-2 of FIG. 1.

FIG. 2 is a cross-sectional view through line 2-2 of FIG. 1, showing additional details of the foot 14. The foot 14 can include a cleaning head 24 having a pivot joint 26 which couples the cleaning head 24 according to the invention to the lower handle assembly 18. The pivot joint 26 can be a universal joint with permits the foot 14 to swivel about multiple axes relative to the lower handle assembly 18. A cleaning cloth 28 through which steam and/or a cleaning fluid is dispensed onto a surface to be cleaned is coupled to a bottom of the cleaning head 24. It is also contemplated that the foot 14 can further comprise an agitator, such as a rotatably mounted brush, or an oscillating or otherwise movable cleaning cloth 28 for agitating and loosening foreign matter, such as dirt, dust and the like. Alternatively, the foot 14 can also include a sweeper assembly provided by a rotatably mounted brush and dirt collection bin for collecting dirt and dust.

The cleaning cloth 28 can be removably coupled with the cleaning head 24 according to any known method. As illustrated, the cleaning cloth 28 is secured to the cleaning head 24 with a drawstring assembly 38 that tightens the cleaning cloth 28 around the cleaning head 24. In another example, the cleaning cloth 28 can be removably coupled with the cleaning head 24 using hook and loop fasteners, an example of which includes VELCRO®. In another example, one or more elastic straps can be used to secure the cleaning cloth 28 to the cleaning head 24. In yet another example, resilient cloth engagement and retention members having a plurality of outwardly radiating slits as is commonly known in the art can be used.

A steam conduit 54 extends through the cleaning head 24 and couples at one end with a nozzle 52. The steam conduit 54 can include a first conduit portion 32 that extend through the pivot joint 26 and a second conduit portion 34, which may be in the form of a hose or flexible tubing that couples the first conduit portion to the nozzle 52. The nozzle 52 is positioned to direct steam or other cleaning fluid toward a steam manifold 36 that distributes the steam or other cleaning fluid over the cleaning cloth 28.

Figure 3:
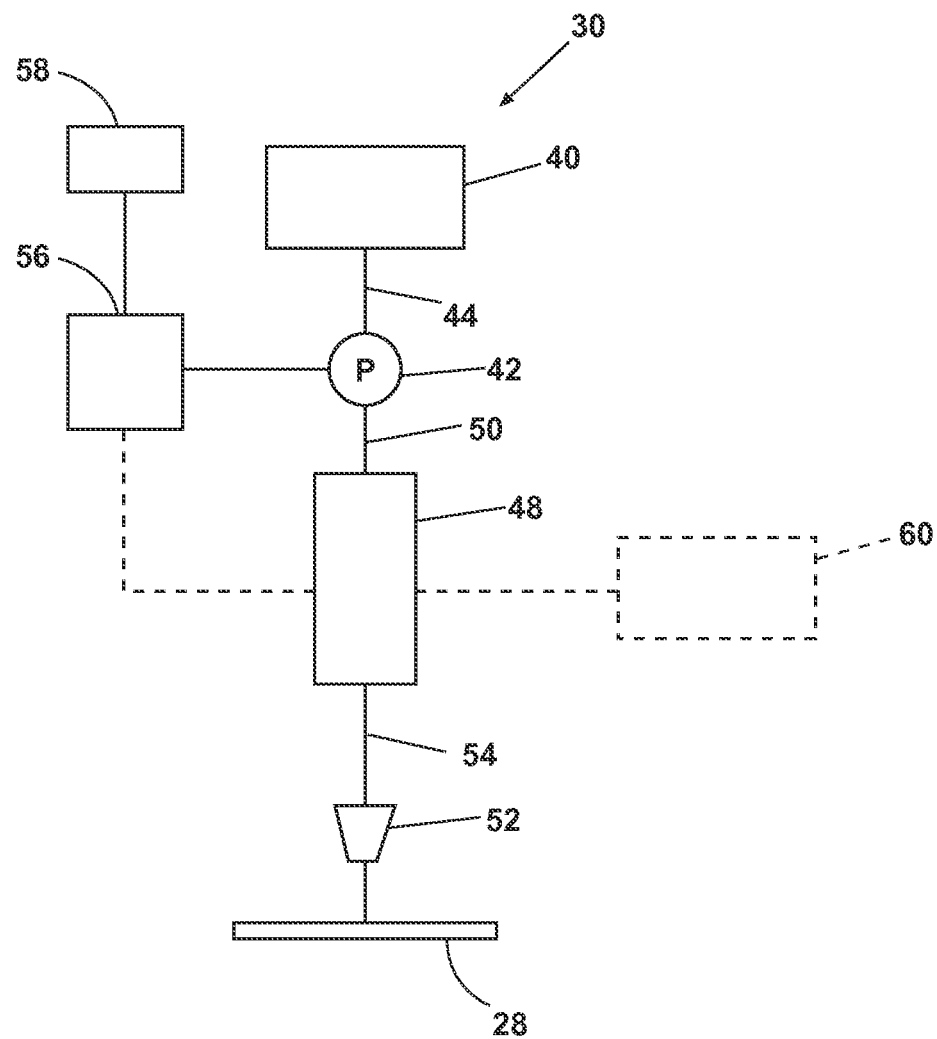
FIG. 3 is a schematic of a fluid distribution system of the upright steam mop of FIG. 1.

FIG. 3 illustrates a schematic of the fluid distribution system 30 which can be used with the steam mop 10 of FIG. 1 for selectively generating and dispensing steam to a surface to be cleaned. The fluid distribution system 30 includes a fluid supply tank 40 for receiving and storing a cleaning fluid. The fluid supply tank 40 can be coupled with a pump 42 by a first fluid conduit 44. The pump 42 can be fluidly coupled with a heating element 48 for heating the fluid from the fluid supply tank 40 to generate steam through a second fluid conduit 50. The heating element 48 can comprise an elongated boiler having an inlet at one end that is fluidly coupled with the pump 42 and an outlet at an opposite end which is fluidly coupled with the nozzle 52 through the steam conduit 54.

The fluid distribution system 30 is controlled by a microswitch 56, which is electrically connected to the pump 42. The steam mop 10 can also include a trigger 58 (FIG. 1) projecting outwardly from the grip assembly 22 for selective actuation by a user. Actuation of the trigger 58 actuates the microswitch 56 of the fluid distribution system 30 for selectively generating and dispensing steam. The microswitch 56 can also be electrically connected to the heating element 48 such that power is also supplied to the heating element 48. Alternatively, a separate actuator 60, shown in phantom line in FIG. 3, can be provided for activating the heating element 48. In yet another configuration, power can be supplied to the heating element continuously when the steam mop 10 is connected to a power source. Depressing the trigger 58 actuates the microswitch 56 and energizes the pump 42 to dispense fluid from the fluid tank 40 to the heating element 48 through the first and second fluid conduits 44 and 50 for selectively generating steam. The steam is delivered from the heating element 48 to the nozzle 52 through the steam conduit 54. The nozzle 52 can be mounted within the cleaning head 24 and configured to dispense steam onto the cleaning cloth 28.

The fluid supply tank 40 can be configured to hold a predetermined amount of liquid. In one embodiment, the liquid is water or electrolyzed water. Optionally, a variety of cleaning chemicals, fragrances, botanical oils, and the like can be mixed with the water. An optional filter module (not shown) can be detachably connected to the fluid supply tank 40 for removing impurities within the cleaning fluid. The fluid supply tank 40 can be provided with a selectively closable opening through which a user can fill the fluid supply tank 40 with the desired liquid.

Figure 4:
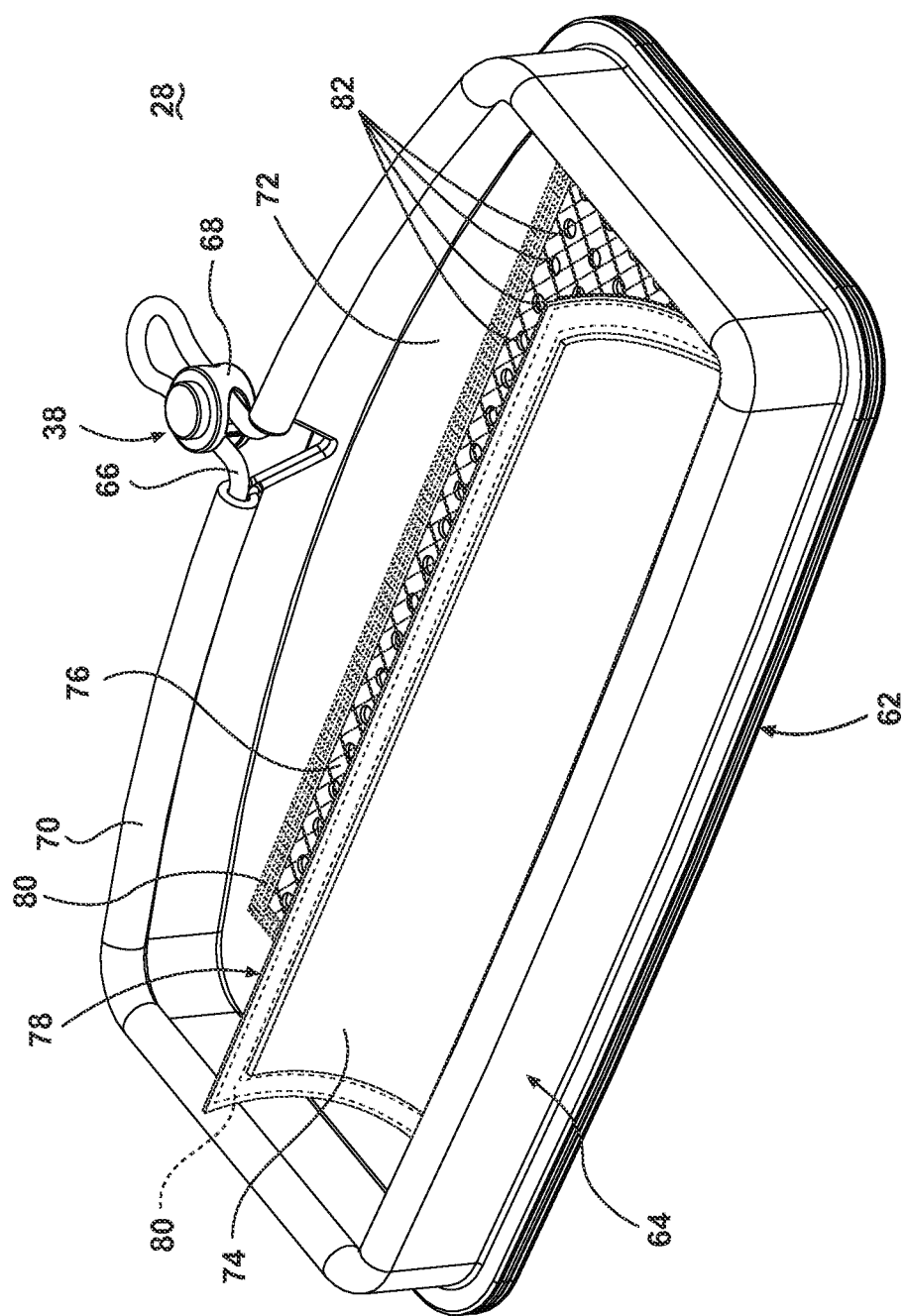
FIG. 4 is a perspective view of a cleaning cloth for use with the upright steam mop of FIG. 1.

FIG. 4 illustrates one embodiment of the cleaning cloth 28 according to the invention. The cleaning cloth 28 includes the drawstring assembly 38, a bottom cloth 62, an edge cloth 64 attached to the bottom cloth 62. The drawstring assembly 38 includes a drawstring cord 66 and a cord lock 68 that attaches to the drawstring cord 66 to tighten the drawstring cord 66. The edge cloth 64 includes a channel 70 through which the drawstring cord 66 extends. The cleaning cloth 28 can be configured to be disposable after one or more uses, or can be washable for reuse.

The bottom cloth 62 can be multi-layered, with at least one lower layer 72 and at least one upper layer 74. The layers 72, 74 can be made from a woven material, such as cotton, or a non-woven material, such as microfiber. At least the lower layer 72 can be textured to provide increased friction between the cleaning cloth 28 and the surface to be cleaned and loosen foreign matter, such as dirt, dust and the like. While the lower and upper layers 72, 74 may each be described herein as a single layer, each may instead include multiple layers of material attached together.

The cleaning cloth 28 can also be provided with a cleaning component 76. The cleaning component 76 can include a disinfecting or sanitizing agent. As used herein, the term "disinfecting or sanitizing agent" is used to refer to any organic or synthetic chemical or chemical composition having anti-bacterial, anti-viral, miticidal, germicidal, anti-fungal and anti-microbial properties. The cleaning component 76 can further or alternatively include a fragrance, an odor-eliminating agent, odor control agents (i.e. Febreze®), and EPA-exempted natural disinfectants, including botanical disinfectants comprising one or more essential oils such as thyme, peppermint, eucalyptus, cinnamon, lemongrass, thyme or other natural oils. The cleaning cloth 28 can also include one or more floor care components, which may or may not be part of the cleaning component 76 to impart additional treatments to enhance the appearance and protection of the flooring surface, such as floor polish (i.e. Mop & Glo®), polymer protectant, anti-streaking components and vinegar, for example.

The cleaning component 76 can be embedded within the bottom cloth 62, such as between the lower and upper layers 72, 74. Alternatively, the cleaning component can be affixed to the top surface of the bottom cloth 62 with dissolvable adhesive such as PVA tape, for example. The cleaning component 76 can be provided in different physical forms, such as in a singular form like a strip or wafer, a granulated form, a dissolvable or rupturable film sachet, or a gel contained within a heat- and/or moisture-soluble capsule. As illustrated in FIG. 4, the cleaning component 76 is provided in strip form. The strip can be provided with one or more perforations or holes 82, which may increase the penetration of steam through the cleaning cloth 28 and/or increase the amount of surface area of the cleaning component 76 that is exposed to the steam.

At least a portion of the upper layer 74 can form a cover 78 for a pocket that receives the cleaning component 76. As illustrated, the cover 78 can be provided with means that allow a user to easily open the cover 78, such hook and loop fasteners 80, an example of which includes VELCRO®. This would permit the user to replenish the cleaning component 76 as necessary. While shown as a flap being separable from the lower layer 72 on at least three sides, it is also possible for the cover 78 to only be separable from the lower layer 72 on one side, thereby permitting a user to slide the cleaning component 76 into the pocket between the lower and upper layers 72, 74. Alternatively, the cover 78 can be sealed around the cleaning component 76 to one of the layers 72, 74 after manufacture, for example when the cleaning cloth 28 is disposable cleaning. The cover 78 can be sealed using any suitable method, non-limited examples of which include stitching or adhesion.

The cleaning component 76 can be embedded within or affixed to the bottom cloth 62 using any suitable method, a non-limiting example of which includes embedding the disinfecting or sanitizing formulation in water-soluble polymer film, which is then applied one or more layers 72, 74 of the bottom cloth 62. The film can be applied by various methods known in the art, such as, but not limited to, thermal bonding, ultrasonic bonding, adhesive bonding (including hot melt adhesive), and laminating. Alternatively, the encapsulated disinfecting or sanitizing formulation can be loosely placed between layers of the cleaning cloth 28. In this case, the layer(s) between the disinfecting or sanitizing formulation and the surface to be cleaned can be made from a moisture penetrative material. In the case of a strip or wafer-form cleaning component 76, the cleaning component 76 can be inserted into the pocket between the lower and upper layers 72, 74, and the cover 78 thereafter closed over the cleaning component 76. In the case of a granulated cleaning component 76, the cleaning component 76 can be sprinkled onto the lower layer 72 or injected between the layers 72, 74.

The cleaning component 76 can include an encapsulated formulation. The formulation can be encapsulated within an encapsulation barrier or capsule. The encapsulation barrier can be selected to rupture dissolve in the presence of moisture and/or heat. Some examples of suitable encapsulation barriers include, but are not limited to, vinyl alcohol-vinyl acetate copolymer, polyvinyl alcohol polymer, and octenylsuccinates-starch polymer. In one embodiment, the encapsulation barrier can comprise a polyvinyl alcohol (PVA) polymer film that is adapted to dissolve when exposed to moisture at or above a certain elevated threshold temperature, for example, 80° C. or higher, such as the temperature required to generate steam. If the threshold temperature is not reached, the film barrier remains intact.

The encapsulated formulation can comprise one or more disinfecting or sanitizing agents. Encapsulation of the disinfecting or sanitizing formulation can prevent degradation of the disinfecting or sanitizing formulation and/or preserve the efficacy of the disinfecting or sanitizing formulation until the time of use. Encapsulation of the disinfecting or sanitizing formulation can also prevent premature reactions with other components embedded within the cleaning cloth 28. Exposure to moisture and/or heat will rupture or dissolve the encapsulation barrier, thereby releasing the disinfecting or sanitizing agents.

Non-limiting examples of suitable disinfecting or sanitizing agents include quaternary ammonium compounds, also known as quats, such as Dialkyl quats, Dialkyl blend quats, been registered and approved by the U.S. Environmental Protection Agency (EPA). Examples of suitable EPA registered formulations are listed in the following table:

| Chemical Composition (Ingredient and Wt %) | | Trade Name | Company | EPA Number |
|---|---|---|---|---|
| Alkyl dimethyl benzyl ammonium chloride ($C_{12-18}$) | 25% | BTC ® 2125M | Stepan Company, Northfield, Illinois | 1839-46 |
| Alkyl Alkyl dimethyl benzyl ammonium chloride ($C_{12-14}$) | 25% | | | |
| Inert ingredients | 50% | | | |
| Alkyl dimethyl benzyl ammonium chloride ($C_{12-18}$) | 40% | BTC ® 2125M-80% | Stepan Company, Northfield, Illinois | 1839-54 |
| Alkyl dimethyl benzyl ammonium chloride ($C_{12-14}$) | 40% | | | |
| Inert ingredients | 20% | | | |
| Alkyl dimethyl benzyl ammonium chloride ($C_{12-18}$ | 20% | BTC ® 2125M P40 | Stepan Company, Northfield, Illinois | 1839-55 |
| Alkyl dimethyl benzyl ammonium chloride ($C_{12-14}$) | 20% | | | |
| Inert ingredients | 60% | | | |
| Alkyl dimethyl benzyl ammonium chloride ($C_{12-18}$) | 25% | Maquat MQ2525M-50% | Mason Chemical Co., Arlington Heights, Illinois | 10324-28 |
| Alkyl dimethyl ethyl benzyl ammonium chloride ($C_{12-14}$) | 25% | | | |
| Ethanol | 2% | | | |
| Water | 48% | | | |
| Alkyl dimethyl benzyl ammonium chloride ($C_{12-18}$) | 40% | Maquat MQ2525M-80% | Mason Chemical Co., Arlington Heights, Illinois | 10324-27 |
| Alkyl dimethyl ethyl benzyl ammonium chloride ($C_{12-14}$) | 40% | | | |
| Ethanol | 10% | | | |
| Water | 10% | | | |
| Alkyl dimethyl benzyl ammonium chloride ($C_{12-16}$) | 20% | Maquat MQ615M | Mason Chemical Co., Arlington Heights, Illinois | 10324-51 |
| Octyl decyl dimethyl ammonium chloride | 15% | | | |
| Dioctyl dimethyl ammonium chloride | 7.5% | | | |
| Didecyl dimethyl ammonium chloride | 7.5% | | | |
| Ethanol | 5-10% | | | |
| Water | 40-45% | | | |
| Didecyl dimethyl ammonium chloride | 50% | Maquat 4450-E | Mason Chemical Co., Arlington Heights, Illinois | 10324-34 |
| Ethanol | 10% | | | |
| Water | 40% | | | |
| Alkyl ($C_{14}$ 50%, $C_{16}$ 10%, $C_{12}$ 40%) Dimethyl Benzyl Ammonium Chloride | 50% | Barquat ® MB-50 | Lonza, Basel, Switzerland | 6836-2 |
| Ethyl alcohol | 10% | | | |
| Water | 40% | | | |
| Alkyl ($C_{14}$ 50%, $C_{16}$ 10%, $C_{12}$ 40%) Dimethyl Benzyl Ammonium Chloride | 80% | Barquat ® MB-80 | Lonza, Basel, Switzerland | 6836-14 |
| Ethyl alcohol | 10% | | | |
| Water | 10% | | | | single-chain quats and dual chain quats, hydrogen peroxide or hydrogen peroxide derivatives, or colloidal particles with disinfecting or sanitizing properties, like silver and/or copper.

The disinfecting or sanitizing formulation can be encapsulated according to any known method. One method of encapsulation includes adding lower molecular weight, waxy maize octenylsuccinates to starch polymer by esterifaction of starch hydroxyl groups with octenylsuccinic anhydride. Another method includes using polyvinyl alcohol to encapsulate the disinfecting or sanitizing formulation. This may be useful in the case of a strip- or wafer-form cleaning component 76.

The encapsulated disinfecting or sanitizing formulation embedded in the cleaning cloth 28 can be one that has already The encapsulated formulation can comprise a fragrance, in addition to or alternatively to one or more disinfecting or sanitizing agents. The fragrance can be encapsulated within an encapsulation barrier or capsule selected to rupture or dissolve in the presence of moisture and heat. Encapsulation of the fragrance can prevent degradation of the fragrance and/or preserve the strength of the fragrance until the time of use. Exposure to moisture and/or heat will rupture or dissolve the encapsulation barrier, thereby releasing the fragrance. The fragrance can be encapsulated using any of the methods discussed herein.

In use, the moisture and heat from the steam distributed through the cleaning cloth 28 by the fluid dispensing system 30 interacts with the encapsulation barrier of the encapsulated formulation embedded within the cleaning cloth 28 to release the formulation onto the surface being cleaned. The moisture and steam can dissolve, melt or otherwise degrade the encapsulation barrier, thus releasing the formulation. Depending on the encapsulation barrier, only moisture or heat may be required to release the formulation. Alternatively, heat and moisture from the steam may be required to release the formulation. Although the cleaning cloth 28 shown in FIG. 4 includes an upper layer 74 forming a cover 78 in the form a flap, pouch or pocket for holding the cleaning component 76, the cover 78 can be omitted altogether and the cleaning component can be affixed directly to the top surface of the bottom cloth 62 as will be described hereinafter. Elements that are common or substantially similar to previously described elements of the invention are identified with the same reference numeral bearing a prime (') symbol.

Figure 5:
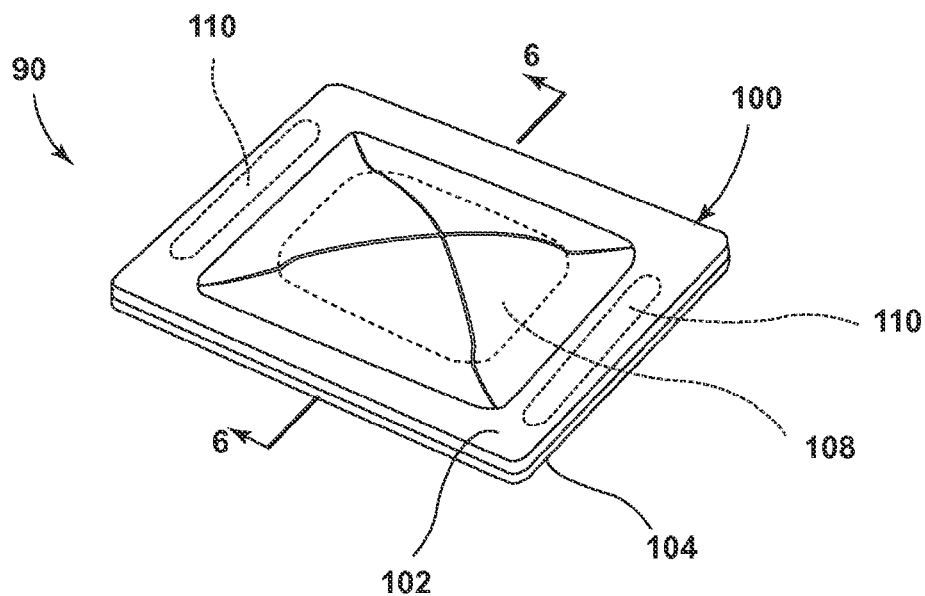
FIG. 5 is a perspective view of a universal cleaning component according to another embodiment of the invention.
Figure 6:
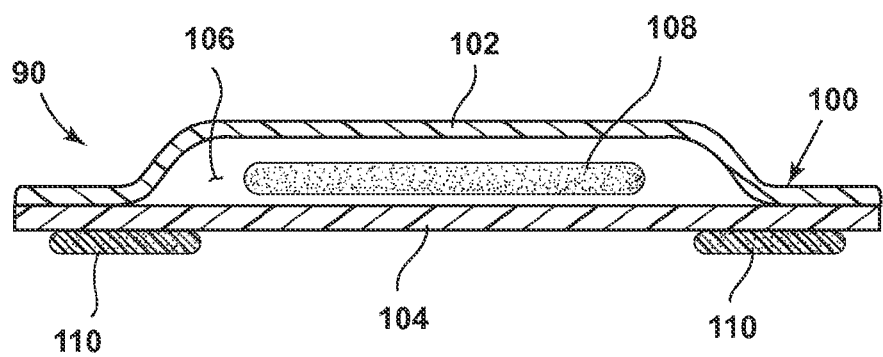
FIG. 6 is a cross-sectional view of the cleaning cloth of FIG. 5 taken along line 6-6 of FIG. 5.

As depicted in FIGS. 5-6, the cleaning component 90 can comprise a universal moisture and heat-soluble sachet 100 that is adapted for use with any cleaning cloth for a steam cleaner. The sachet 100 can comprise a top layer 102 and bottom layer 104 formed of moisture-soluble PVA film that is configured to dissolve over time upon exposure to at least one of moisture and heat. Alternatively, the top and bottom layers can be formed out of high temperature moisture-soluble PVA film configured to dissolve upon exposure to steam. The top and bottom layers 102, 104 are sealed around the perimeter of the sachet 100 forming a cavity 106 therebetween for receiving a variety of consumable materials, such as fragrance or a wide array of cleaning ingredients as previously described. The consumable materials can be provided in the form of a wafer insert 108 comprising anhydrous material such as powder, soap film or paper soap sheet encapsulated between the top and bottom layers 102, 104. The wafer insert 108 can be infused with one or more of a fragrance and a variety of cleaning compositions such as surfactants, oxygenated components, anti-streaking components, shine components or polymer protectant for example. Alternatively, materials such as fragrance can be provided in the form of anhydrous oil drops inserted between the top and bottom layers 102, 104 of the sachet 100.

As shown in FIGS. 5-6, a moisture-soluble adhesive 110, such as PVA tape, can be secured to the bottom surface of the sachet 100. The adhesive 110 can include a user-removable liner (not shown) that a user can remove to expose the adhesive tape prior to affixing the sachet to the top surface of the bottom cloth 62. The sachet 100 can be positioned on the bottom cloth 62 so that it is exposed to the steam distributor nozzle 52 when the cleaning cloth 28 is mounted to the foot 14. Accordingly, the cleaning component 90 can be easily affixed to any cleaning cloth for a steam cleaner. Alternatively, the sachet 100 can be inserted into a pouch, pocket, or separable flap formed on the top of the bottom cloth as previously described.

In operation, steam flows through the distributor nozzle 52 and contacts the cleaning component 90. The steam dissolves the top and bottom layers 102, 104 of the sachet 100 as well as the adhesive 110 and eventually exposes the wafer insert 108 therein. The wafer insert 108 and material infused therein are dissolved into the cleaning cloth 28 and as the cloth becomes saturated with steam, the ingredients of the cleaning component 90 are distributed onto the surface to be cleaned or into the ambient atmosphere. Because the top and bottom layers 102, 104 and adhesive 110 are all configured to dissolve over time upon exposure to steam, a user does not have to contact the soiled cleaning cloth 28 to remove and dispose the cleaning component 90 prior to laundering the cleaning cloth 28.

Figure 7:
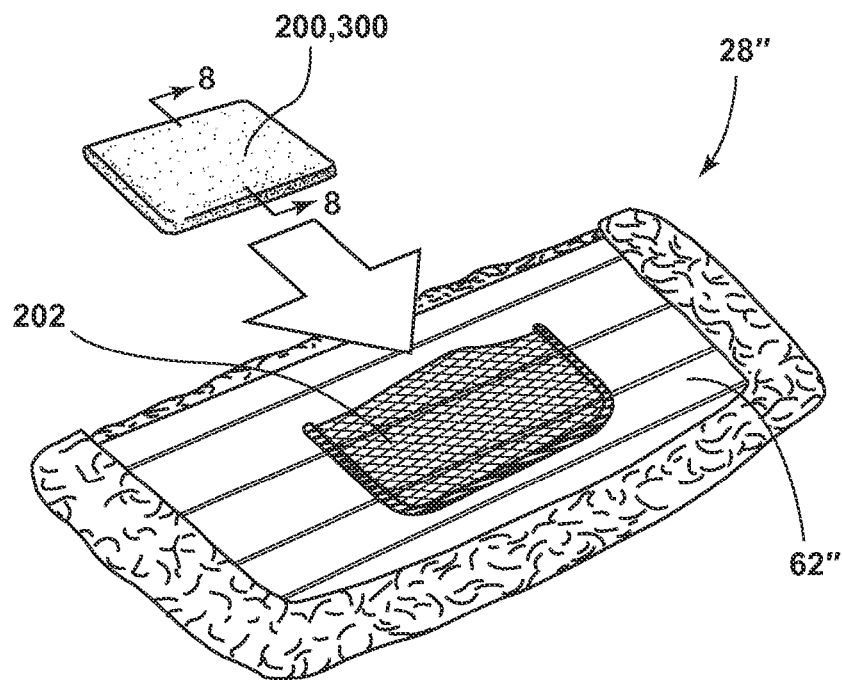
FIG. 7 is an exploded, perspective view of a cleaning component and cleaning cloth according to another embodiment of the invention.

In another embodiment of the invention shown in FIG. 7, the cleaning component 190 can comprise a wafer 200 that is formed of fragrance-infused thermoplastic concentrate such as polyethelyne (PE), polypropylene (PP), or polyvinyl chloride (PVC). Elements that are common or substantially similar to previously described elements of the invention are identified with the same reference numeral bearing a double prime (") symbol. The wafer 200 can comprise a variety of shapes and sizes. In one embodiment the wafer 200 can comprise a thin, flexible injection-molded rectangular card akin to a conventional credit card. The wafer 200 can be inserted into a pouch 202, pocket, or separable flap formed on the top of the bottom cloth 62" as previously described. Alternatively, the wafer 200 can be removably coupled to either of the cleaning cloth 28" or cleaning head 24 by any suitable attachment means such as hook and loop fasteners, or a temporary or removable adhesive, for example.

In operation, steam flows through the distributor nozzle 52 and contacts the wafer 200. Heat and moisture from the steam accelerates the release and volatilization of the infused fragrance from the wafer 200 into the cleaning cloth 28" and surrounding atmosphere. The infused fragrance can be configured to last for one or more cleaning operations, but will eventually diminish to a negligible level. The user can replace the spent wafer with a fresh wafer to renew emission of the consumable during use.

Figure 8:
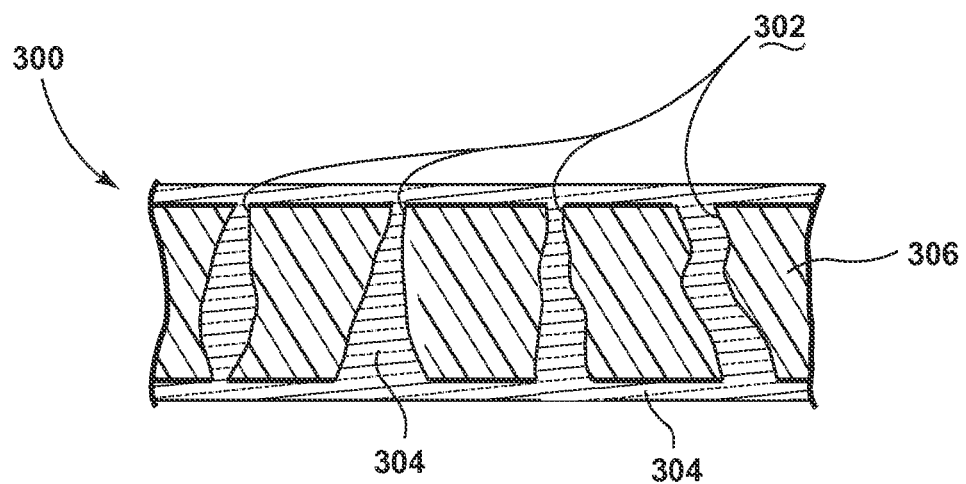
FIG. 8 is a cross-sectional view of a cleaning component according to another embodiment of the invention.

In yet another embodiment illustrated in FIG. 8, a wafer 300 can comprise a porous film 306 formed of thermoplastic sheet material of polyethylene (PE), polypropylene (PP) or polyvinylidene fluoride (PVDF), for example. A plurality of pores 302 are dispersed throughout the film 306. Pore sizes can range from approximately 10 to 150 microns. The wafer 300 can further comprise a coating 304 such as a liquid or gel fragrance, which saturates the pores. The coating 304 can optionally further comprise a variety of additional cleaning ingredients as previously described. Optionally, the wafer 300 can comprise a useful life indicator. For example, the fragrance can comprise a color tint that contrasts with the wafer substrate material, which can be white or transparent. Fragrance dissipates during use and thus exposes an increasing area of the color contrasting wafer substrate, thereby indicating the remaining useful life of the wafer.

In operation, steam flows through the steam distributor nozzle 52 and contacts the wafer 300. Heat or a combination of heat and moisture from the steam volatilizes the coating 304 and releases it from the pores 302 and surface of the film 300 into the cleaning cloth and surrounding atmosphere. The coating can be configured to have a useful life of one or more cleaning tasks, but will eventually diminish to a negligible level. For example, the coating can comprise a fragrance that gradually diminishes during use. The fragrance can be color-tinted so that it progressively fades and exposes an increasing area of the color contrasting wafer substrate, until the color dissipates completely and the entire wafer film 306 is exposed. Accordingly, the wafer 200, 300 and color-tinted fragrance coating are adapted to provide an end of useful life indicator that signals a user to replace the wafer with a fresh, unused wafer.

While the invention has been specifically described in connection with certain specific embodiments thereof, it is to be understood that this is by way of illustration and not of limitation, and the scope of the appended claims should be construed as broadly as the prior art will permit. Reasonable variation and modification are possible within the foregoing specification and drawings without departing from the spirit of the invention, which is set forth in the accompanying claims.

What is claimed is:

1. A cleaning cloth for use with a steam mop having a housing mounting the cleaning cloth for cleaning the surface to be cleaned and a steam delivery system for delivering steam to the cleaning cloth, the cleaning cloth comprising:
   at least one fabric layer that is configured to be attached to a steam mop; and
   an encapsulated cleaning composition associated with the fabric layer and configured to be released from the encapsulation by exposure to steam delivered to the cleaning cloth.

2. A cleaning cloth according to claim 1 wherein the at least one fabric layer comprises two fabric layers that form a pocket and the encapsulated cleaning composition is positioned in the pocket.

3. A cleaning cloth according to claim 2 wherein the at least one fabric layer further comprises a cover for closing an opening to the pocket.

4. A cleaning cloth according to claim 1 wherein the encapsulated cleaning composition is embedded within or attached to the at least one fabric layer.

5. A cleaning cloth according to claim 1 wherein the encapsulated cleaning composition comprises a cleaning composition embedded within a water-soluble polymer film, which is mounted to the at least one fabric layer.

6. A cleaning cloth according to claim 5 wherein the film is mounted by one of thermal bonding, ultrasonic bonding, adhesive bonding, hot melt adhesive, dissolvable adhesive, or laminating.

7. A cleaning cloth according to claim 1 wherein the at least one fabric layer comprises a lower fabric layer and an upper fabric layer, and the encapsulated cleaning composition is positioned between the upper and lower fabric layers.

8. A cleaning cloth according to claim 7 wherein the lower fabric layer is textured to increase friction with the surface to be cleaned.

9. A cleaning cloth according to claim 8 wherein the upper fabric layer is joined with the lower fabric layer and at least one edge of the upper fabric layer is separable from the lower layer.

10. A cleaning cloth according to claim 9 wherein the upper fabric layer forms a flap that includes a hook and loop fastener between the lower fabric layer and the upper fabric layer.

11. A cleaning cloth according to claim 1 wherein the encapsulated cleaning composition comprises a disinfecting or sanitizing agent having anti-bacterial, anti-viral, miticidal, germicidal, anti-fungal or anti-microbial properties.

12. A cleaning cloth according to claim 11 wherein the disinfecting or sanitizing agent comprises an EPA-exempted natural disinfectant.

13. A cleaning cloth according to claim 11 wherein the disinfecting or sanitizing agent comprises one of: quaternary ammonium compounds (quats), such as Dialkyl quats, Dialkyl blend quats, single-chain quats or dual chain quats, hydrogen peroxide or hydrogen peroxide derivatives, or colloidal particles with disinfecting or sanitizing properties, silver colloidal particles or copper colloidal particles.

14. A cleaning cloth according to claim 1 wherein the encapsulated cleaning composition comprises at least one of a fragrance, an odor-eliminating agent, or an odor control agent.

15. A cleaning cloth according to claim 14 wherein the encapsulated cleaning composition further comprises at least one floor care component selected from the group comprising floor polish, polymer protectant, anti-streaking components, or vinegar.

16. A cleaning cloth according to claim 1 wherein the encapsulated cleaning composition is bonded, affixed or in register with the at least one fabric layer.

17. A cleaning cloth according to claim 16 wherein the encapsulated cleaning composition is embodied in a film, a wafer, a pouch, a sachet, or a granulated composition.

18. A cleaning cloth according to 17 wherein the wafer is a fragrance-infused thermoplastic sheet and the fragrance is volatilized into the cleaning cloth and surrounding atmosphere when the sheet is exposed to steam.

19. A cleaning cloth according to claim 1 wherein the encapsulated cleaning composition comprises a wafer, and the wafer comprises multiple perforations to pass steam through the cleaning composition.

20. A cleaning cloth according to claim 19 wherein the wafer is a porous plastic sheet and the cleaning composition is released from the perforations into the cleaning cloth and surrounding atmosphere when the wafer is exposed to steam.

21. A cleaning cloth according to claim 1 wherein the encapsulated composition comprises a gel contained within a heat- and/or moisture-soluble barrier.

22. A cleaning cloth according to claim 21 wherein the barrier comprises one of vinyl alcohol-vinyl acetate copolymer, polyvinyl alcohol polymer, or octenylsuccinates-starch polymer.

23. A cleaning cloth according to claim 1 wherein the encapsulated cleaning composition is released only upon reaching a temperature of at least about 80° C.

24. A steam mop comprising a housing for movement along a surface to be cleaned; a cleaning cloth according to claim 1 coupled with the housing for cleaning the surface to be cleaned; and a steam delivery system for delivering steam to the cleaning cloth.

25. A steam mop according to claim 24 wherein the housing comprises a foot assembly for movement along a surface to be cleaned and a handle assembly mounted to the foot assembly, and wherein the cleaning cloth is mounted to the foot assembly.

26. A method for cleaning a surface comprising:
   applying to the surface a cleaning cloth with a cleaning composition encapsulated within a heat-activated barrier; and
   delivering steam to the cleaning cloth to release the cleaning composition from within the heat-activated barrier for application onto the surface.

27. The method of claim 26 wherein the cleaning composition is applied to the cleaning cloth by the act of embedding, thermal bonding, ultrasonic bonding, adhesive bonding, hot melt adhesive, dissolvable adhesive, or laminating.

28. The method of claim 26 and further comprising dissolving, melting or degrading the barrier to release the cleaning composition onto the surface.

* * * * *